US008838637B2

(12) United States Patent
Ho et al.

(10) Patent No.: US 8,838,637 B2
(45) Date of Patent: Sep. 16, 2014

(54) SYSTEMS AND METHODS FOR PROCESSING CONSUMER QUERIES IN DIFFERENT LANGUAGES FOR CLINICAL DOCUMENTS

(75) Inventors: Kinson Kin Sang Ho, Waterloo (CA); Ge Yu, Waterloo (CA)

(73) Assignee: AGFA Healthcare Inc., Toronto (CA)

( * ) Notice: Subject to any disclaimer, the term of this patent is extended or adjusted under 35 U.S.C. 154(b) by 235 days.

(21) Appl. No.: 12/703,479

(22) Filed: Feb. 10, 2010

(65) Prior Publication Data

US 2011/0196886 A1    Aug. 11, 2011

(51) Int. Cl.
*G06F 19/00* (2011.01)

(52) U.S. Cl.
CPC ............ *G06F 19/322* (2013.01); *G06F 19/321* (2013.01)
USPC .......................................................... 707/760

(58) Field of Classification Search
USPC ............................................... 707/760; 705/2
See application file for complete search history.

(56) References Cited

U.S. PATENT DOCUMENTS

| 8,027,970 | B1 * | 9/2011 | Brette et al. ................... 707/713 |
| 2005/0091424 | A1 * | 4/2005 | Snover et al. ................... 710/33 |
| 2005/0229158 | A1 * | 10/2005 | Thusoo et al. ................ 717/115 |
| 2007/0107033 | A1 | 5/2007 | Ho et al. |
| 2007/0136345 | A1 * | 6/2007 | Blazejewski et al. ......... 707/101 |
| 2008/0208625 | A1 | 8/2008 | Joseph |
| 2008/0253693 | A1 | 10/2008 | Chu et al. |

OTHER PUBLICATIONS

International Search Report dated Jul. 1, 2011 for International Application No. PCT/EP2011/051581.

(Continued)

*Primary Examiner* — Amresh Singh
(74) *Attorney, Agent, or Firm* — Bereskin & Parr LLP; Isis Caulder (57) ABSTRACT

A computer implemented method of performing at least one document consumer query using a processor and a memory coupled to the processor, said method comprising the steps of: receiving at least one query for at least one clinical documents in a first query language from at least one document consumer; translating the query into a second query language to obtain a translated query; conducting the translated query in at least one database compatible with the second query language by the processor to obtain a first result; and providing the obtained first result to the document consumer. In some embodiments, the first query language is Digital Imaging and Communications in Medicine (DICOM) language, or the Hypertext Transfer Protocol (HTTP) language, and the second language is Cross-Enterprise Document Sharing (XDS) language.

24 Claims, 4 Drawing Sheets

(56) References Cited

OTHER PUBLICATIONS

Written Opinion of the International Search Authority for International Application No. PCT/EP2011/051581, Dated: Jul. 1, 2011.
H Nelken: Cross Enterprise Document Sharing—A Standards-based Solution for National Level Document Sharing:, 2006, pp. 1-8, XP055000270, Sector Technical Institute, Montpelier Retrieved from the Internet: URL:http://www.research/ibm.com/jam/STI_XDS.pdf.
Bill Majurski: "IT Infrastructure: Profiles for Health Information Exchange", National Institute of Standards and Technology (NIST), Aug. 20, 2008, pp. 1-145, XP055000273, Retrieved from the Internet: URL:http://ihexds.nist.gov/XdsDocs/slides/xds_20080715.ppt.
IHE International: IHE IT Infrastructure Technical Framework, vol. 2b, Transactions Part B—Sections 3.29-3.43, Aug. 10, 2009, XP055000429, Retrieved from the Internet: URL:http://www.ihe.net/Technical_Framework/upload/IHE_ITI_TF_6-0_Vol2b_FT_2009-08-10.pdf.
IHE International: "IHE IT Infrastructure Technical Framework, vol. 3, Cross-Transaction Specifications and Content Specifications", Aug. 10, 2009, XP055000426, Retrieved from the Internet: URL:http://www.ihe.net/Technical_Framework/upload/IHE_ITI_TF_6-0_vol3_FT_2009-08-10.pdf.

* cited by examiner

SYSTEMS AND METHODS FOR PROCESSING CONSUMER QUERIES IN DIFFERENT LANGUAGES FOR CLINICAL DOCUMENTS

FIELD

The invention relates generally to the field of data storage systems and particularly to the field of data storage systems within the medical industry.

BACKGROUND

The field of medical information systems has been an expanding field for several decades. With increasing diagnostic tools, increasing population, more wide-spread access to medical treatment, and the desirability of sharing information between doctors and professionals, the field of medical information systems is likely to continue growing. To address this continued growth, and the subsequent inconveniences of paper and other fixed forms of clinical documents storage, the medical community has increasingly turned to digital forms of clinical document management.

To facilitate digitalization of clinical documents, the medical industry has created a number of standards and languages for managing clinical documents. Such standards typically integrate clinical documents generated by medical hardware from multiple manufacturers. These standards facilitates managing and sharing of documents amongst various entities in the industry such as a private physician's office to a clinic to an acute care in-patient facility and other personal health record systems. However, there are varying standards being used in the industry, and varying standards may not be necessarily compatible with one another, and a system created in accordance with one standard may not be compatible with another system created in accordance with another standard.

A document consumer may need to search and retrieve data from multiple datacenters. However, each datacenter is independent, self-contained, and may not be able to directly communicate with other datacenters. Instead, each datacenter may communicate with a network control hub to share and obtain information from other datacenters. This configuration may also be viewed as a hub and spoke configuration wherein the hub is the control center to where each datacenter (spokes) are linked.

Another problem a document consumer may face when searching and retrieving data from multiple datacenters is that data in various datacenters may not be in the same format as in the document consumer. For example, the serial number in one domain could be in a six-digit format (e.g. 123456) while in another domain, the serial number may be alpha-numeric (e.g. AB1111). In another example, the patient identification number assigned to a particular patient may be different in various datacenters.

Another problem a document consumer may face when searching and retrieving data from multiple datacenters is the datacenters may not be compatible with the syntax that the document consumer operates. For example, the document consumer may be operating in a first language and the datacenter in a second language, and the first language and the second language are not compatible with one another.

Accordingly there is a need for a method, a system and/or an apparatus that addresses at least some of the concerns in the existing prior art.

SUMMARY

According to one embodiment, there is provided a computer implemented method of performing at least one document consumer query comprising: providing a processor and a memory operatively coupled thereto, receiving at least one query for at least one clinical documents in a first query language from at least one document consumer at the processor, translating the query into a second query language to obtain a translated query by the processor, conducting the translated query in at least one database compatible with the second query language by the processor to obtain a first result, and providing the obtained first result to the document consumer.

In some embodiments, wherein the first query language is one of the following languages: Digital Imaging and Communications in Medicine (DICOM) language, and Hypertext Transfer Protocol (HTTP) language, and the second language is Cross-Enterprise Document Sharing (XDS) language.

In some embodiments, wherein when the query in the first language comprises a patient identifier containing at least one wildcard, the method further comprises performing at least one of searching the memory for a uniquely linked patient identifier and truncating the at least one wildcard from the patient identification information, such that a patient identifier without any wildcards is obtained, querying an external cross-referencing engine using the patient identifier without any wildcards to determine whether there is a unique match between the patient identifier without any wildcards and a patient identifier in the external cross-referencing engine, and if a unique match is found, using the patient identifier in the external cross-referencing engine to translate the query.

In some embodiments, wherein when the query contains at least one DICOM attribute constraint, and the translation of the query into a second query language comprises at least one of the following mappings: direct one-to-one mapping from the at least one DICOM attribute to a corresponding XDS attribute; concatenating a number of different a plurality of the DICOM attributes to a corresponding XDS attribute; associating the at least one DICOM attribute to a set of values, the result of the association being indicative of a corresponding XDS attribute; and specifying a fixed value for the corresponding XDS attribute.

In some embodiments, wherein when the database contains objects compatible and incompatible to the at least one document consumer, conducting the translated query further comprises selecting compatible objects to be returned as the first result.

In some embodiments, wherein when the query is for an imaging object, and the database contains metadata about a plurality of clinical documents of various types including imaging objects, conducting the translated query further comprises selecting metadata associated with clinical documents which are imaging documents to be returned as the first result.

In some embodiments, wherein when the first results comprises metadata about clinical documents, the method further comprises storing the metadata in the memory such that the metadata is available locally for at least one future query.

In some embodiments, wherein when the first result comprises metadata about clinical documents, the method further comprising receiving a retrieve request in the first language for requested clinical documents comprising at least one clinical document from the document consumer based on the first result; and performing the retrieve request in the second language such that the clinical document requested is provided to the document consumer.

In some embodiments, wherein when the requested clinical documents are stored in at least one database external to the consumer proxy, the method further comprising: determining whether a data communication link exists between the external database and the document consumer; and based on the results of the determination, performing at least one of directing the external database to return the requested clinical documents to the document consumer directly if the communication link exists, and retrieving the requested clinical documents at the consumer proxy and then providing the requested clinical documents to the document consumer if the communication link does not exist.

In yet another embodiment, there is provided a physical computer readable medium stored with a program for causing a computer processor to function as a consumer proxy for processing document consumer queries for patient data in one or more databases comprising: receiving at least one query for at least one clinical documents in a first query language from at least one document consumer, translating the query into a second query language to obtain a translated query, conducting the translated query in at least one database compatible with the second query language by the processor to obtain a first result, and providing the obtained first result to the document consumer.

In yet another embodiment, there is provided a consumer proxy for performing at least one document consumer query comprising a processor, a memory operatively coupled to the processor, wherein the processor is programmed for: receiving at least one query for one or more clinical documents in a first query language from at least one document consumer; translating the query into a second query language to obtain a translated query; conducting the translated query in at least one database compatible with the second query language by the processor to obtain a first result; and providing the obtained first result to the document consumer.

In some embodiments, wherein the first query language is one of the following languages: Digital Imaging and Communications in Medicine (DICOM) language, and Hypertext Transfer Protocol (HTTP) language, and the second language is Cross-Enterprise Document Sharing (XDS) language.

In some embodiments, wherein when the query in the first language comprises a patient identifier containing at least one wildcard, the processor is further programmed for performing at least one of searching the memory for a uniquely linked patient identifier and truncating the at least one wildcard from the patient identification information, such that a patient identifier without any wildcards is obtained, querying an external cross-referencing engine using the patient identifier without any wildcards to determine whether there is a unique match between the patient identifier without any wildcards and a patient identifier in the external cross-referencing engine, and if a unique match is found, using the patient identifier in the external cross-referencing engine to translate the query.

In some embodiments, wherein when the query contains at least one DICOM attribute constraint, and the translation of the query into a second query language comprises at least one of the following mappings, direct one-to-one mapping from the at least one DICOM attribute to a corresponding XDS attribute, concatenating a number of different a plurality of the DICOM attributes to a corresponding XDS attribute, associating the at least one DICOM attribute to a set of values, the result of the association being indicative of a corresponding XDS attribute, and specifying a fixed value for the corresponding XDS attribute.

In some embodiments, wherein when the database contains objects compatible and incompatible to the at least one document consumer, the processor is further programmed for selecting compatible objects to be returned as the first result.

In some embodiments, wherein the query is for an imaging object, and the database contains metadata about a plurality of clinical documents of various types including imaging objects, the processor is further programmed for selecting metadata associated with clinical documents which are imaging documents to be returned as the first result.

In some embodiments, wherein when the first results comprises metadata about clinical documents, the processor is further programmed for storing the first results in the memory such that the metadata is available locally for at least one future query.

In some embodiments, wherein when the first result comprises metadata about clinical documents, the processor is further programmed for
receiving a retrieve request in the first language for requested clinical documents comprising at least one clinical document from the document consumer based on the first result, and performing the retrieve request in the second language such that the clinical document requested is provided to the document consumer.

In some embodiments, wherein when the requested clinical documents are stored in at least one database external to the consumer proxy, the processor is further programmed for: determining whether a data communication link exists between the external database and the document consumer; and based on the results of the determination, performing at least one of: directing the external database to return the requested clinical documents to the document consumer directly if the communication link exists, and retrieving the requested clinical documents at the consumer proxy and then providing the requested clinical documents to the document consumer if the communication link does not exist.

In yet another embodiment, there is provided a system for processing at least one document consumer query comprising: at least one document consumer operating in a first language having a processor programmed for submitting at least one query for clinical documents in the first language; at least one document registry operating in a second language incompatible with the first language, the document registry having a memory containing metadata about clinical documents whereby the query is to be conducted; at least one consumer proxy comprising a memory and a processor coupled thereto, the processor programmed for receiving the query from the document consumer, translating the query into the second language to obtain a translated query compatible with the database, conducting the translated query in the second language at the database to obtain a first result containing metadata about clinical documents, and providing the first results to the document consumer.

In some embodiments, the first language is one of the following languages: Digital Imaging and Communications in Medicine (DICOM) language, and Hypertext Transfer Protocol (HTTP) language, and the second language is Cross-Enterprise Document Sharing (XDS) language.

In some embodiments, the system further comprising an external cross-referencing engine and wherein when the query in the first language comprises a patient identifier containing at least one wildcard, the processor in the consumer proxy is further programmed for performing at least one of searching the memory for a uniquely linked patient identifier and truncating the at least one wildcard from the patient identification information, such that a patient identifier without any wildcards is obtained, querying the external cross-referencing engine using the patient identifier without any wildcards to determine whether there is a unique match between the patient identifier without any wildcards and a patient identifier in the external cross-referencing engine, and if a unique match is found, using the patient identifier in the external cross-referencing engine to translate the query.

In some embodiments, wherein when the database contains objects compatible and incompatible to the at least one document consumer, the processor is further programmed for selecting compatible objects to be returned as the first result.

In some embodiments, wherein when the requested clinical documents are stored in at least one database external to the consumer proxy, the processor in the consumer proxy is further programmed for determining whether a data communication link exists between the database and the document consumer, based on the results of the determination, doing at least one of directing the database to return the requested clinical documents to the document consumer directly if the at least one communication link exists, and retrieving the requested clinical documents at the consumer proxy and then providing the requested clinical documents to the document consumer if the at least one communication link does not exist.

DRAWINGS

For a better understanding of the embodiments described herein and to show more clearly how they may be carried into effect, reference will now be made, by way of example only, to the accompanying drawings which show at least one example embodiment, and in which.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

The embodiments of the systems and methods described herein may be implemented in hardware or software, or a combination of both. However, preferably, these embodiments are implemented in computer programs executing on programmable computers each comprising at least one processor, a data storage system (including volatile and non-volatile memory and/or storage elements), at least one input device, and at least one output device. For example and without limitation, the programmable computers may be a mainframe computer, server, personal computer, laptop, personal data assistant, or cellular telephone. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer, for configuring and operating the computer when the storage media or device is read by the computer to perform the procedures described herein. The inventive system may also be considered to be implemented as a computer-readable storage medium, configured with a computer program, where the storage medium so configured causes a computer to operate in a specific and predefined manner to perform the functions described herein.

Figure 1:
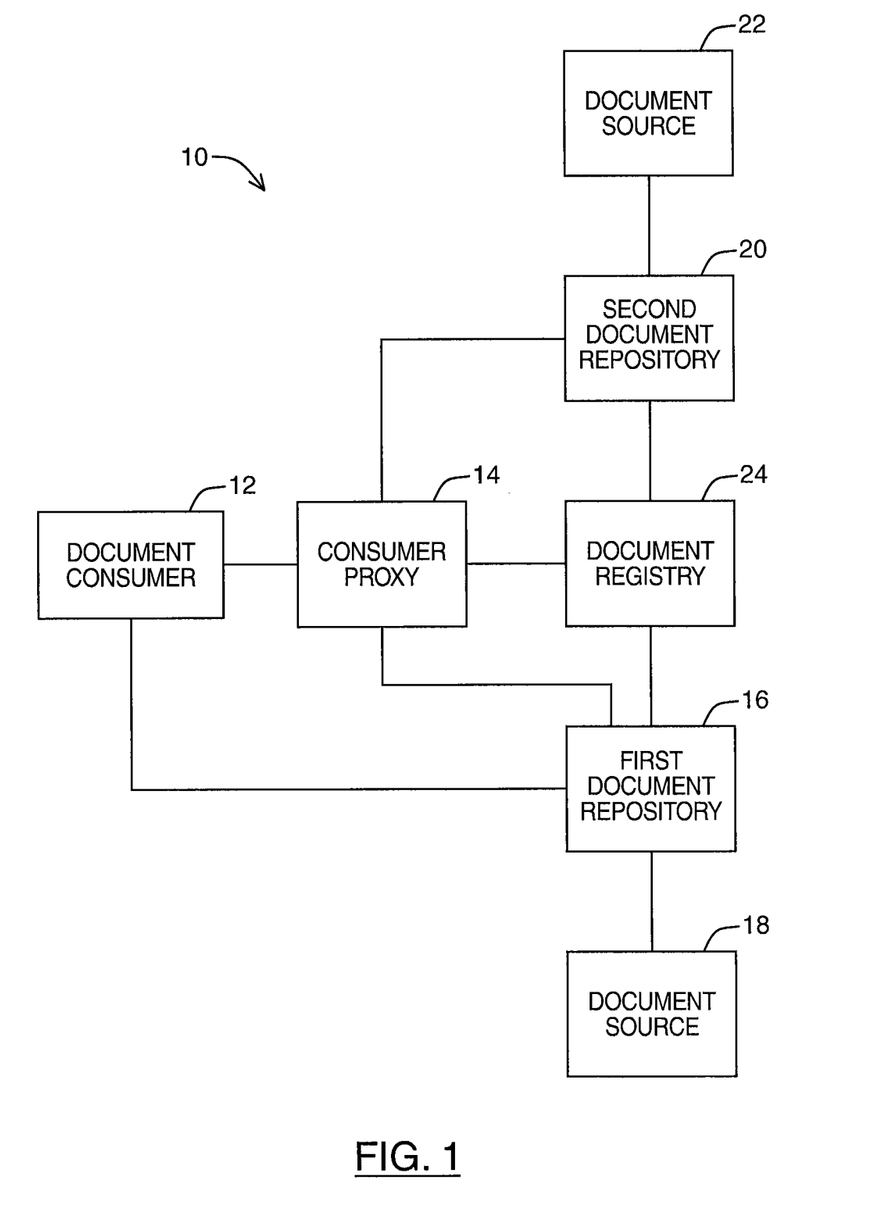
FIG. 1 is schematic representation of a consumer proxy system according to the embodiments described herein.

Reference is made to FIG. 1, which illustrates the components of a consumer proxy system made in accordance with an exemplary embodiment. The consumer proxy system 10 comprises a document consumer 12, consumer proxy 14, a first document repository 16, a second document repository 20, a document source 18, a document source 22 and a document registry 24. The system 10 is described herein to contain a certain number of elements, namely, one document consumer 12, one consumer proxy 14, two document repositories 16 and 20, two document sources 18 and 22 and one document registry 24. However, the number of these elements contained within a system might differ in other embodiments. For example, there could be more than one or more datacenters and more than one document source which may be connected to any, some or all of the document repositories. Similarly, there could also be more than one document consumer and document registry. In some embodiments, the document repository and the document source may be combined into one entity.

The document consumer 12 may be any entity that may wish to search for and retrieve one or more clinical documents. For example, a user of the document consumer 12 may be a medical professional or any other interested party with appropriate security access level who may be desirous of obtaining one or more clinical documents relating to a patient. For example, a document consumer 12 may be a health care professional working at an in-patient facility. In another example, a document consumer 12 may be a specialist working at an out-patient facility. In another example, a document consumer 12 may be a long-term care facility. The document consumer 12 may also be a non-human entity. For example, a document consumer 12 may be a clinical IT software that wishes to retrieve a clinical document for its own records. Document consumer 12 may be implemented using various computers including but are not limited to, personal computers, laptop computers, slim line computers, server based computers, handheld computers, and any other such device that is able to provide an interface and connect to the consumer proxy 14 through a communication network. Each document consumer 12 may have an output device (not shown) such as a monitor or screen associated with it for viewing of the medical document and/or for engaging with the displayed medical document, and an input device (not shown) for receiving input from one or more users of the document consumer 12.

Document consumer 12 will typically run a clinical document management system compatible with one or more standards. Such standards in the industry may include Digital Imaging and Communications in Medicine (DICOM) standard. The DICOM standard facilitates communications between systems by providing a communication protocol and common file formats. It enables integration of hardware components such as scanners, servers, workstations, printers, and network hardware from multiple manufactures into a picture achieving and communication system. The invention will be described herein with the document consumer 12 operating in the DICOM standard, and the clinical document that it wishes to obtain is image data in a file compatible with the DICOM format. In other embodiments, other standards, such as Hypertext Transfer Protocol (HTTP) may be used.

As shown in FIG. 1, document consumer 12 is in direct data communication with the consumer proxy 14, and the first document repository 16. In other embodiments, the document consumer 12 may be connected directly with the document registry and/or any of the document repositories.

The first document repository 16 and the second document repository 20 are responsible for persistent storage of clinical documents. The first document repository 16 and document repository 20 have memory for storage of the clinical documents and a processor coupled to the memory. The first document repository 16 and document repository 20 may also have back-up systems for disaster recovery purposes. For example, the first document repository 16 and document repository 20 may have memory organized in Redundant Array of Independent Disks (RAID) standard to promote data resiliency. Periodical backups of the memory in the first document repository 16 and document repository 20 may be performed and the back up copy may be stored at a different geological location from the first document repository 16 and document repository 20.

The first document repository 16 and the second document repository 20 may utilize database software to organize and store the clinical documents in the memory. The database software may organize the clinical documents according to various database architectures. For example, the clinical documents may be stored as a relational database. However, the first document repository 16 and the second document repository 20 need not use database software. For example, the first document repository 16 and the second document repository 20 may store the clinical documents in the memory without using any database software.

The first document repository 16 and second document repository 20 operate in a standard different from that of the document consumer 12. The standard may not be compatible with the communication protocol used by the document consumer 12 such that the consumer 12 may not access the contents of the document repositories 16, 20.

The first document repository 16 and the second document repository 20 in the embodiment as shown are configured in a Cross-Enterprise Document Sharing (XDS) standard defined by Integrating the Health care Enterprise (IHE), which publishes technical specifications. In other embodiments, the document repository 16 and/or 20 may be configured in any standard that is different from and incompatible with the standard employed by the document consumer 12.

The first document repository 16 and the second document repository 20 are in data communication with the document source 18 and the document source 22 respectively. The first document repository 16 and document repository 20 receive clinical documents and associated metadata from the document source 18 and document source 22 respectively for persistent storage.

Document source 18 and document source 22 generate clinical documents and metadata about the clinical documents. Document source 18 and document source 22 may be a combination of hardware and software components. Document source 18 and document source 22 may be an acquisition source (i.e. modality), generating one or more clinical documents. For example, the document source 18 and document source 22 may be medical imaging instruments such as an X-ray, ultrasound, magnetic resonance, positron emission tomography, computed tomography, endoscopy, mammograms, digital radiography, and cardiology machines. The document source 18 and document source 22 may also be other systems such as picture archiving and communication systems (PACS). The document source 18 and document source 22 may also include human actors. For example, an ultrasound system will generally contain a hardware component, a software component and a medical professional to operate the system.

A clinical document contains information pertaining to an individual patient, and it may be image data or non-image data. The information contained in the clinical document could be medical and/or non-medical in nature. For example the information contained in a clinical document may be medical in nature such as an X-Ray image of a patient's wrist or a doctor's diagnosis of the patient. The information may also be non-medical in nature such as biographical information, contact information or emergency contact information. A clinical document may be generated in a clinic, hospital, or other entities contributing to an individual's health and well-being. For example, a clinical document generated by an insurance company may contain insurance information such as the name of the insurer and the insurance policy number. Generally, a clinical document contains information about an individual that a health provider may wish to consider.

A clinical document may be formatted to work with various software. For example, a clinical document may be formatted to comply with Adobe published document format (PDF). In another example, a clinical document may be an image formatted to comply with Digital Imaging and Communications in Medicine (DICOM) standard. In another example, the clinical document may be in a Health Level 7 Clinical Document Architecture (HL7 CDA) format that is used to define clinical information such as medical summary, diagnostic report, discharge summary and, lab report.

A document source may also convert clinical documents from one format to another prior to transmittal and/or storage. For example, an image document in JPEG format might be converted into PDF format prior to transmittal and/or storage. While clinical documents may be of varying formats, XDS systems generally only store PDF format documents, text documents, or patient manifests. Clinical documents that are not PDF, text or manifests may be converted to one of these formats.

A clinical document may also be compressed by a document source prior to transmittal and/or storage to reduce the size of the document. Compressing algorithms that may be used to compress clinical documents may include lossy or lossless variants of the JPEG format for images, as well as a lossless Run-Length Encoding format, which is similar to the packed-bits of compression found in some TIFF format images. Other compression algorithms may also be used.

Each document source 18 and document source 22 may generate DICOM manifests, which contains information about the clinical documents. The manifest may indicate what objects are of interest for related clinical documents. An exemplary manifest may include any combination of: a manifest identifier comprising an universally unique identifier (UUID), a patient identifier for an affinity domain, a patient name, a repository unique identifier, and a list of associated clinical documents, and corresponding one or more pointers relating to that list. The list of clinical documents comprises metadata about the clinical documents, but not the clinical documents themselves. The pointers include information to identify a location whereby a clinical document corresponding to the pointer may be retrieved. The manifest identifier is unique to the system. A system-wide unique number can be generated by incorporating a time variable and ensure that the clock between the components of the system are synchronized. Aside from a time variable, there might also be other components that guarantee that the UUID is globally unique as will be evident to one skilled in the art.

Each document source 18 and document source 22 may also generate metadata along with the clinical document and/or the manifest. Metadata will contain information about the clinical document and/or the manifest. For example, metadata may contain biographical information about the subject patient such as the patient's name, age, and gender. The metadata information may also contain information about the clinical document such as the type of scan, image dimensions, and/or the type of document source used to generate the clinical document, Metadata may also contain references to one or more clinical documents. For example, metadata may contain a hyperlink to reference the image as a DICOM Web Access of DICOM Objects (WADO) URI or as IHE Retrieve Information for Display (RID) request for document.

The document source 18 and 22 will transmit the generated clinical document and the manifest to the document repository 16 and 20 respectively for persistent storage. The metadata may be sent along with the clinical document in a single file. For example, a single DICOM file contains both the metadata as well as all of the image data. The metadata may also be sent in a separate file from the document. For example, the Analyze format stores the image data in one file, ending with the extension ".img" and the metadata in another file, ending with the extension ".hdr".

The document repository 16 and 20, which are operating in XDS standard may append additional XDS metadata to the manifest that describes the manifest. For example, the document repositories 16 and 20 may also add additional XDS metadata about the manifest such as the hash code and repository unique identification number.

The first document repository 16 and the second document repository 20 are in data communication with document registry 24. Each document repository 16 and document repository 20 transmits metadata to the document registry 24. That is, the document repository 16 and 20 stores the received clinical documents, manifests and metadata in its memory, and transmits associated metadata to the document registry.

The document registry 24 receives metadata associated with the clinical documents and manifests stored in the first document repository 16 and document repository 20. In the embodiment as shown, which is operating in accordance with IHE XDS standard, the clinical documents and manifests themselves are not provided to the document registry 24, and only the metadata is provided. However, in another embodiment, some clinical documents may be provided to the document registry 24. For example, document registry 24 may wish to store frequently requested clinical documents for caching purposes.

The document registry 24 may organize and store received metadata using database software. Since the document registry 24 acts as the primary search venue, it may organize received patient manifests to optimize searching performance. The document registry 24, and the first document repository 16 and document repository 20 are configured to operate in a standard that is not compatible to that of the document consumer 12.

The document consumer 12 may wish to search for clinical documents related to a patient that may be stored in the first document repository 16 or document repository 20. Since the document consumer 12 is configured to operate in accordance with the DICOM standard, it generates appropriate query command in DICOM language, which may be a "CFind" command. The document consumer 12 is not directly connected to the document registry 24 or the second document repository 20, and may not submit the query to them directly. Document consumer 12 is directly connected with the first document repository 16. However, since document consumer 12 and the first document repository 16 are configured in different standards, DICOM and XDS respectively, document repository 20 will not able to process queries in DICOM language submitted by the document consumer 12. For similar reasons, even if document consumer 12 is connected to the document registry 24 directly, they will not be able to communicate to facilitate searches.

The consumer proxy 14 facilitates communications between document consumer 12 and document registry 24, document repository 16 and document repository 20, which are operating in different standards and languages. In the embodiment as shown, the consumer proxy 14 is in data communication with document consumer 12 and document registry 24, document repository 16 and document repository 20. In other embodiments, the consumer proxy 14 may not be in direct communication with the first and/or second document repositories 16, 20.

The consumer proxy 14 comprises a processor and a memory coupled to the processor. For example, the consumer proxy 14 could be personal computers, laptop computers, slim line computers, server based computers, handheld computers. The consumer proxy 14 may store clinical documents, metadata relating to the clinical documents such as patient manifests, and/or translated queries as described herein below.

The processor in the consumer proxy 14 is configured to receive a query in a first language, which in this embodiment is the DICOM syntax. The received query is translated to a second language, which is in a XDS-compatible syntax. The differences between the standards do not permit perfect translation between the languages. In particular, not all attributes specified in the DICOM CFind query can be transformed, and the consumer proxy 14 will perform a best effort transformation.

A best effort transformation may support various types of mappings between DICOM attribute and XDS attributes. A best effort transformation may support direct one-to-one mapping from a DICOM attribute to a corresponding XDS attribute. It may support a combination mapping that concatenate a number of different DICOM attributes to a corresponding XDS attribute. It may map a DICOM attribute to a set of values and the result is used for the corresponding attribute. It may employ a combination of the above mappings based on a list of preference for the corresponding XDS attribute. It may also specify a fixed value for the corresponding XDS attribute. A reverse of the mapping may be performed when mapping an XDS attribute back to a DICOM attribute.

Even with a best effort transformation, the consumer proxy 14 may not be able translate all possible DICOM CFind queries. For example CFind queries without a specific patient identifier (hereinafter "patient ID") may not be translated to corresponding XDS queries. If wildcards are used within the patient ID, the wildcards must be resolved prior to translating the query to the XDS-compatible format.

The consumer proxy 14 may facilitate wildcard searches on patient ID for the incoming DICOM CFind requests by attempting to resolve the wildcards. The XDS query requires a patient ID in an affinity domain for a search to be conducted.

An affinity domain in XDS is a domain, which there only exists one document registry, one or more document repositories, document sources and consumers. A unique affinity domain patient ID is used to reference the same patient between different components within the domain. The affinity domain patient ID may be different from the local patient ID, which may be unique to a particular component such as a specific hospital. Accordingly when a patient ID received in a search request is not a patient ID in the affinity domain, it is necessary to find the associated patient ID in the affinity domain.

The affinity domain patient ID could be obtained by querying an external cross-referencing engine (not shown) using the received local patient ID as the constrain. The external cross referencing engine may be a software module that is capable of identifying and linking different patient IDs belonging to a same individual patient. For example, the external cross-referencing engine may be the Patient Identifier Cross-referencing (PIX) Manager as defined in IHE ITI PIX Profile. The PIX Manager receives patient information from various health care facilities and determines which patient IDs are associated with a same patient.

The cross-referencing engine such as the PIX manager may only support queries for specific patient ID without any wildcards. The processor consumer proxy 14 is programmed to perform the steps described herein below to resolve wildcards contained in the patient ID of received DICOM queries from the consumer 12. Upon receipt of a DICOM query with a wildcard, the processor in the consumer proxy 14 will search the local memory for any patient ID that is uniquely linked to the received patient ID with wildcards. If a unique match is found, the matching patient ID, which has no wildcards, is used to query the cross-referencing engine. If there is more than one match, or if there is not a match, then the processor will consider the location of the wildcards in the search term. If the wildcards are located at the beginning and/or end of the search term, then they are omitted, and the truncated patient id without the wildcards is used to query the cross-referencing engine. If the wildcards are not at the beginning and/or the end (i.e. in the middle) of the search term, then the processor will indicate to the document consumer that a translation cannot be performed. These steps are further elaborated in method 130 as described herein below.

The external cross-referencing engine receives the search term without wildcards from the consumer proxy 14 and determines if there exists a unique match for the search term. If a unique match exists, the cross-referencing engine returns the match to the consumer proxy 14. Alternatively, if there is no unique match, the cross-referencing engine will inform the consumer proxy 14 that there is no unique match. If a unique match to the submitted search term is returned to the consumer proxy 14, the consumer proxy will use the unique match as the patient ID and translate the received DICOM query to an XDS query.

The processor in the consumer proxy 14 is further programmed to conduct the translated query in XDS syntax. The query may be conducted locally and remotely. To conduct the query locally, the processor may search the memory in the consumer proxy 14 as the memory may store metadata associated with clinical documents returned by previously performed searches as described below. The processor will also transmit the translated query remotely to the document registry 24. By conducting the query at the document registry 24, it will effectively query the contents of document repository 16 and document repository 20 since the document repositories metadata relating to clinical documents and manifests stored in their memory to the document registry 24.

If the search in the document registry 24 finds corresponding metadata, the corresponding metadata from the document registry will be retrieved from the memory of the document registry 24 and returned to the consumer proxy 14. The metadata may relate to various types of clinical documents, including clinical documents that are not imaging documents compatible with the DICOM standard on the document consumer 12.

The document consumer 12 in this embodiment operates in the DICOM standard, and is only interested in DICOM compatible imaging documents. The consumer proxy 14 will select metadata relating to DICOM compatible imaging documents from the received metadata and return the selected metadata to the document consumer 12. The consumer proxy 14 may also store the selected metadata corresponding to the search in its memory to attempt to facilitate future queries locally. The clinical documents referred to by the stored selected metadata may be marked as "externally retrievable" and associated external location addresses stored locally.

In some cases, the consumer proxy 14 may not find any metadata corresponding to the query in the document registry 24 and in the local memory of the consumer proxy. In such cases, the consumer proxy may return results indicating that there are no results that match the criteria provided in the query. In some cases, the query submitted by the document consumer 12 may not be processed because the consumer proxy 14 is unable to translate the DICOM query to a XDS query. In such cases, the consumer proxy 14 may return results indicative of its inability to translate the submitted query such that a document consumer 12 may be prompted to submit a new rephrased query. The response to the query, regardless of the content of the response, is returned to the document consumer 12 in a standard that is compatible with the document consumer 12.

The document consumer 12 will review the results of the query returned the consumer proxy 14. If metadata related to clinical documents is returned, the document consumer 12 will review the metadata and select clinical documents that it wishes to obtain. The selection is communicated to the consumer proxy 14 in the form of a retrieve request in the DICOM language.

Consumer proxy 14 will receive the retrieve request in the DICOM language for selected clinical documents from the document consumer 12. The consumer proxy 14 will review the stored search results to determine the location of the documents requested by the consumer 12. The consumer proxy 14 determines whether there exists a direct data communication link between the document consumer 12 and the document repositories 16 and or 20 where the desired clinical documents are stored. The existence of a direct communication link may effect how the document is returned to the document consumer 12.

For example, if the clinical documents are stored in the first document repository 16, then the document consumer 12 is in direct data communication with the first document repository 16 even though document consumer 12 may not be able to directly perform searches on the first document repository 16 due to varying standards. Since document repository 16 and consumer 12 are in data communication, the consumer proxy 14 will send a retrieve request to the first document repository 16 to send the desired clinical documents to the document consumer 12 directly ("3-point move").

Alternatively, if the desired clinical documents are stored in the second document repository 16, then there is no direct communication link between the document consumer 12 and the second document repository 16. In such a case, the consumer proxy 14 will send a retrieve request to document repository 20, and request it to send the desired clinical documents back to the consumer proxy 14. The consumer proxy 14 will then forward the desired clinical documents to the document consumer 12. Since the 3-point move requires less processing and is able to return to the document consumers more quickly, it is preferred that the 3-point move be used if possible.

While the consumer proxy 14 described above conduct searches on XDS metadata, it is also possible for the consumer proxy in some embodiments to search for other document types such as documents in Portable Document Format (PDF) and Clinical Document Architecture (CDA) formats. Received results may be converted into DICOM embedded PDF or CDA format prior to returning the results to the document consumer 12. Such conversation could be performed by the consumer proxy 14, or by the document repository storing the documents.

The communication links described hereinabove may be facilitated locally through a local area network (LAN) or through a wide area network (WAN) such as the Internet. They may also be facilitated using a combination of local area networks and wide area networks. Each of the document consumer 12, consumer proxy 14, document repository 16, document repository 20, document source 18, document source 22 and registry 24 comprises necessary networking hardware such as an Ethernet network card to facilitate data communication. Appropriate security measures, such as encrypting the data, may be applied as necessary to reduce accessibility of the clinical document and metadata by non-authorized entities when data is being transmitted.

Figure 2:
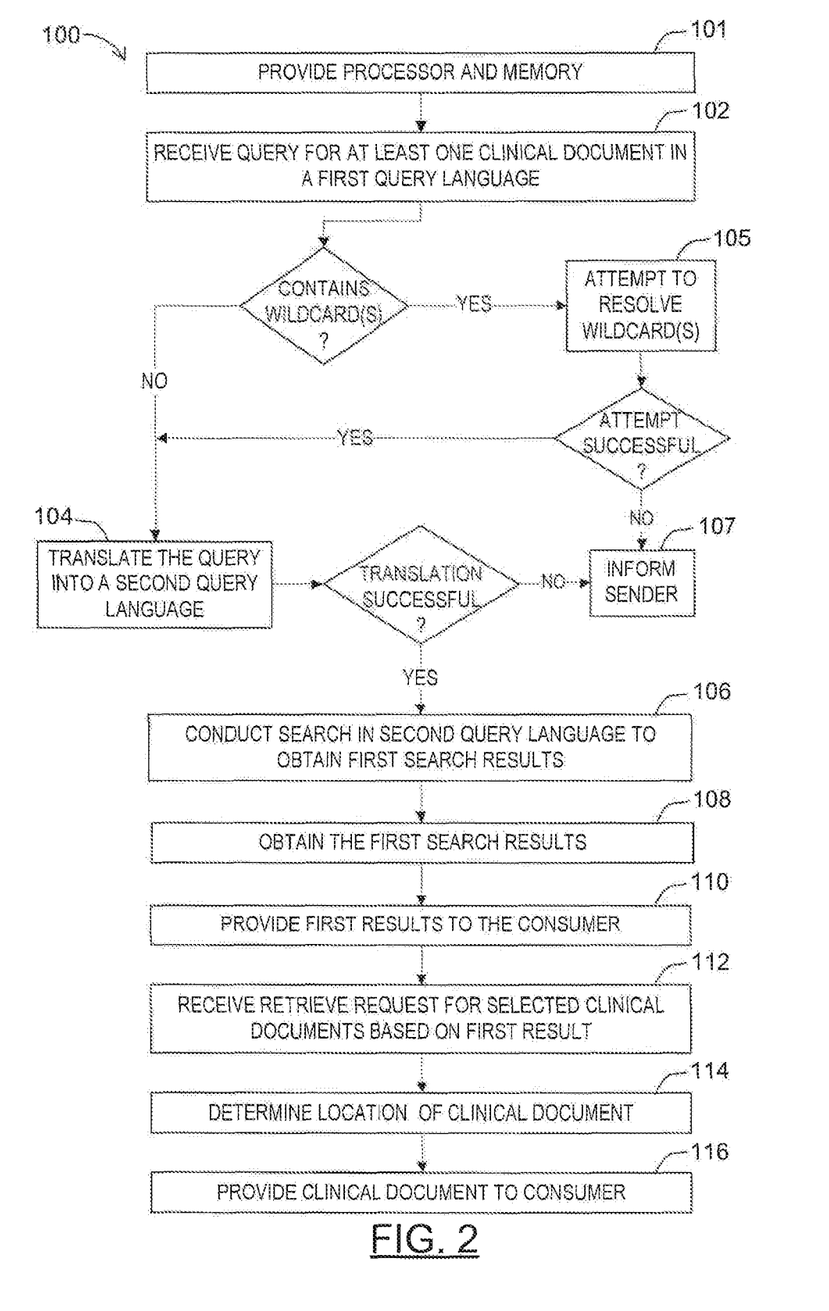
FIG. 2 is a flowchart illustrating the steps of a method of processing at least one document consumer query in a consumer proxy according to the embodiments described herein.

Referring now to FIG. 2, illustrated therein is a flowchart containing the steps for a computer implemented method 100 of processing at least one document consumer query in a consumer proxy according to another embodiment of the invention.

At step 101 a processor and a memory operatively coupled to thereto is provided. The processor is used to perform at least one of the other steps in this method. The memory may be used to store necessary instructions to program the processor to perform at least one of the other steps in this method and/or to store information necessary to perform at least one of the steps of this method.

At step 102, the consumer proxy receives a query for at least one clinical document relating to a patient in a first query language from the at least one document consumer. The document consumer may be any computing device that is able to connect to the consumer proxy, and may be similar to the document consumer 12 described hereinabove in the embodiment shown in FIG. 1. The clinical document may be similar to the clinical document as described hereinabove in the embodiment shown in FIG. 1. The document consumer is operating in the DICOM standard, and the query is for one or more DICOM compatible clinical documents. As such the first query language is in accordance with DICOM standard.

The method 100 proceeds to step 104 where the received patient information query in a first language is translated into a second query language by the processor. A second language may be syntax for another standard different from the first query language. In this embodiment, the second query language is a XDS compatible language. However, there may exist differences between the first query language and the second query language such that a perfect translation between the languages is not possible. For example, the differences between the DICOM and XDS standards do not permit perfect translation between the languages. In particular, not all attributes specified in the DICOM query can be transformed, and the consumer proxy 14 will perform a best effort transformation.

A best effort transformation may support various types of mappings between DICOM attribute and XDS attributes. A best effort transformation may support direct one-to-one mapping from a DICOM attribute to a corresponding XDS attribute. It may support a combination mapping that concatenate a number of different DICOM attributes to a corresponding XDS attribute. It may map a DICOM attribute to a set of values and the result is used for the corresponding attribute. It may employ a combination of the above mappings based on a list of preference for the corresponding XDS attribute. It may also specify a fixed value for the corresponding XDS attribute.

Even with a best effort transformation, the consumer proxy 14 may not be able translate all possible DICOM queries. For example DICOM CFind queries without a specific patient identifier (hereinafter "patient ID") may not be translated to corresponding XDS queries. If wildcards are used within the patient ID, the wildcards must be resolved prior to translating the query to the XDS-compatible format.

Additionally, a query in XDS format requires a patient ID in an affinity domain for a search to be conducted. The affinity domain patient ID could be obtained by querying an external cross-referencing engine (not shown) using the local patient ID as the constraint. However, the cross-referencing engine may only support queries for specific patient ID without any wildcards.

Figure 3:
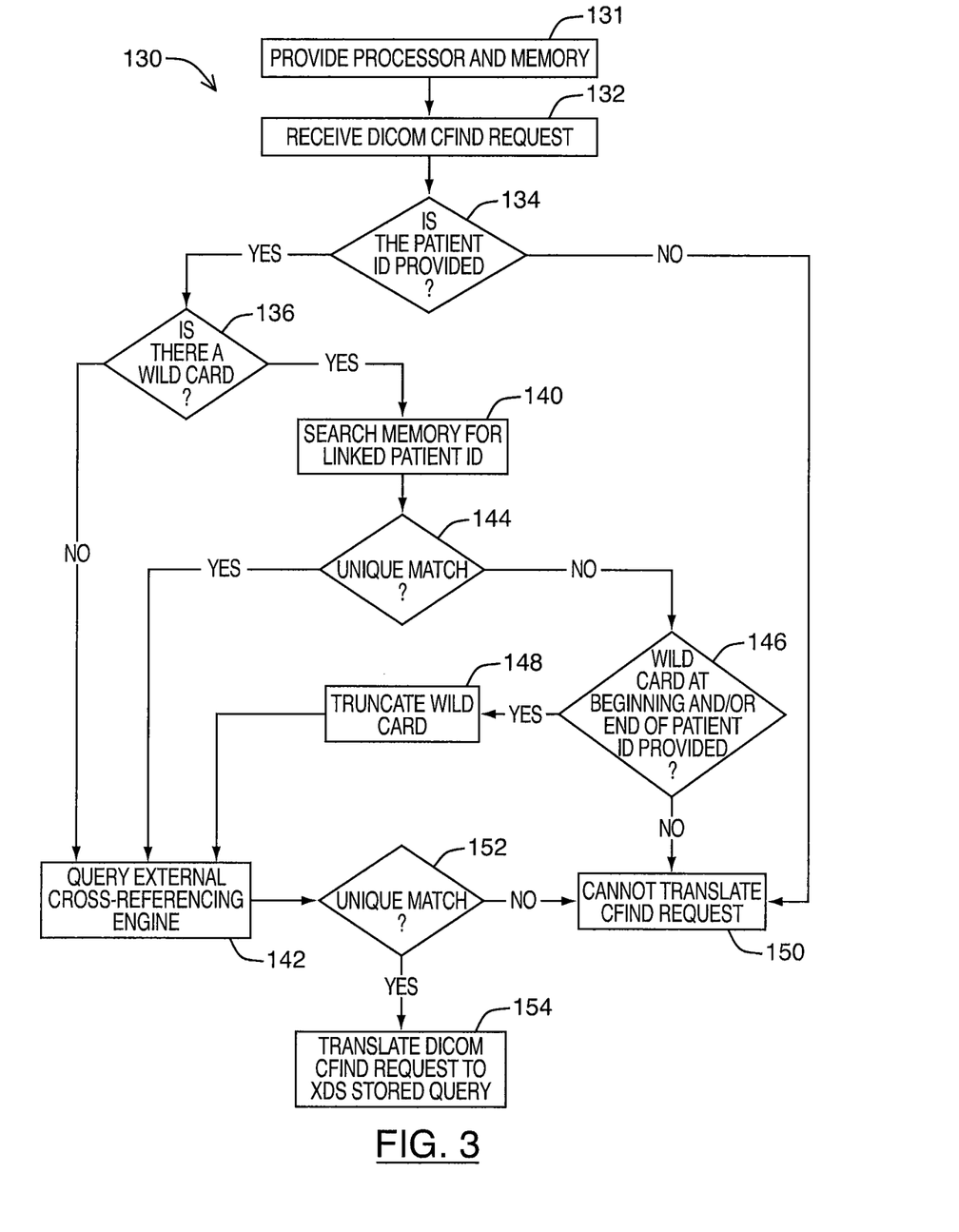
FIG. 3 is flowchart illustrating the steps of a method of translating a DICOM CFind request to a XDS Stored Query according to the embodiments described herein.

If the DICOM query contains wildcards, the consumer proxy will attempt to resolve the wildcards in step 105. At least some of the steps described in method 130 herein below may be used to attempt to resolve wildcards in step 105. If the DICOM query does not contains wildcards, or the attempt to resolve the wildcards in step 105 was successful, the method 100 proceeds to step 104. If the attempt to resolve the wildcards in step 105 was unsuccessful, the method 100 proceeds to step 107.

If the consumer proxy is able to translate the received DICOM query to a corresponding XDS query, the method 100 proceeds to step 106. Alternatively, if the consumer proxy was unable to translate the received DICOM query, then the method 100 proceeds to step 107 whereby the sender of the query is informed that the translation cannot be completed. The translation may not be completed for at least the reasons that there is no patient ID provided, or if the patient ID provided has wildcards that cannot be resolved in step 105.

In step 106, method 100 conducts a search using the query in the second query language, which in this case is the XDS query. The search may be conducted both locally at the memory of the consumer proxy and remotely at a document registry. The document registry may be similar to the document registry 24 described hereinabove. The processor may search the memory in the consumer proxy 14 initially as the memory may store metadata associated with clinical documents returned by previously performed searches. The processor will also transmit the translated query to the document registry to search the document registry. By searching the document registry, it is effectively searching through the contents of one or more document repositories that the document registry is connected to. Document repositories may be similar to the document repositories 16 or 20 described hereinabove.

In step 108, method 100 obtains search results to the XDS query. The results may be obtained from the local memory and/or remote document registry. The search results may contain metadata associated with clinical documents that are not compatible with the document consumer. In such cases, the received metadata will be filtered such that only metadata associated with clinical documents that are compatible with or are interested in by the document consumer are selected.

If the search of the remote document registry returns corresponding metadata, it may be stored in the memory of the consumer proxy to attempt to facilitate future queries locally. For example, the metadata associated with selected DICOM compatible clinical documents may be stored. The clinical documents referred to by the stored metadata may be marked as "externally retrievable" and their associated external addresses stored to facilitate future retrieve requests on the metadata.

In step 110, method 100 provides the results selected in step 108 to the document consumer. In situations where the results are in a format that is not compatible with the document consumer, the processor may further convert the results into a format that is compatible with the document consumer operating in a first language. In some cases, the results of the search may not contain any data if no clinical documents corresponding to the query are found. In other cases, the results of the search may indicate that a query cannot be processed because the processor in the consumer proxy was unable to translate the DICOM CFind query to a XDS query. Yet in other cases, the search results may contain metadata on a list of available clinical documents relating to a patient. The consumer may react to the search results by not responding, submitting another query for another set of results, or by sending retrieve request for one or more clinical documents associated with the metadata in the search result.

The document consumer may review the results and may request specific clinical documents of interest. If the document consumer requests at least one desired clinical document relating to a patient, the method 100 proceeds to step 112.

At step 112, the consumer proxy receives a retrieve request for the desired clinical document from the document consumer.

At step 114, the consumer proxy determines the location of the desired clinical document. The location of the desired clinical document may be determined from the results of the initial query as the metadata associated with the clinical documents generally contains information about where the clinical documents are stored. The existence of a directly communication link may effect how the document is returned to the document consumer at step 116.

At step 116, the processor provides the desired clinical document to the document consumer. How the processor facilitates this query depends on whether there exists a direct data communication link between the document consumer and a document repository where the desired clinical document is stored. If the desired clinical document is located in an external document repository that is in direct data communication with the document consumer, the processor in the consumer proxy will send a retrieve request in the second language such that the desired clinical documents are sent directly to the document consumer ("3-point move"). If there is no direct data communication, then the processor in the consumer proxy will send the retrieve request in the second language such that the desired clinical documents are sent to the consumer proxy. The desired clinical documents are then forwarded to the document consumer. It is preferred that the 3-point move be utilized when possible.

Referring now to FIG. 3, illustrated there in is a computer-implemented method 130 to translate DICOM CFind Request into a XDS Stored Query using a processor and a memory connected to the processor according to one embodiment of the invention.

The method 130 begins at step 132 where the processor receives a DICOM CFind request. At step 134, the processor determines whether there is a patient ID provided in the DICOM CFind request. If a patient ID is not provided, the DICOM CFind request cannot be translated, and the method 130 proceeds to step 150. If a patient ID is provided by the DICOM CFind request, the method 130 proceeds to step 136.

At step 136, it is determined whether one or more wildcards exist within the provided patient ID. If there are no wild cards within the patient ID, the method 130 proceeds to step 142. Alternatively, if there are one or more wildcards in the patient ID, then the method 130 proceeds to step 140.

At step 140, the processor searches the local memory for one or more patient IDs that correspond to the patient ID received from the DICOM request. The method 130 then proceeds to step 144.

At step 144, the processor determines whether if there is a unique match that corresponds to the patient ID received from the DICOM request. If a unique match is found, then the method 130 proceeds to step 142. Alternatively, if a unique match is not found by the search, method 130 proceeds to step 146.

At step 146, the processor determines whether the one or more wildcards are at the beginning and/or end of the patient ID provided. If the one or more wild card is at the beginning or end of the patient ID provided, the method 130 proceeds to step 148. If the one or more wild card is not at the beginning or the end of the patient ID provided, the method 130 proceeds to step 150.

At step 148, the processor truncates the one or more wildcards from the received patient ID. The method 130 proceeds to step 142.

At step 142, the processor will query the external cross-referencing engine using the received patient ID without any wildcards. The patient ID as received may not have originally contained any wildcards (i.e. from step 136), or the contained wildcards have been resolved either by finding a unique linked patient ID in the memory at step 144, or by truncating the wildcard(s) from the patient ID at step 148. The method 130 proceeds to step 152.

At step 152, it is determined where there is a unique match in the external cross-referencing engine for the submitted patient ID without any wildcards. If there is a unique match, the method 130 proceeds to step 154. If there is no unique match, the method proceeds to step 150.

At step 150, the method 130 informs the user that it cannot translate the received patient ID. Inability to translate may result if there is no patient ID provided in the received DICOM request, or if a patient ID provided contains a wildcard, which cannot be resolved by querying the external cross-referencing engine.

At step 154, the unique patient ID in the affinity domain is used to translate the CFind request to XDS stored query.

Figure 4:
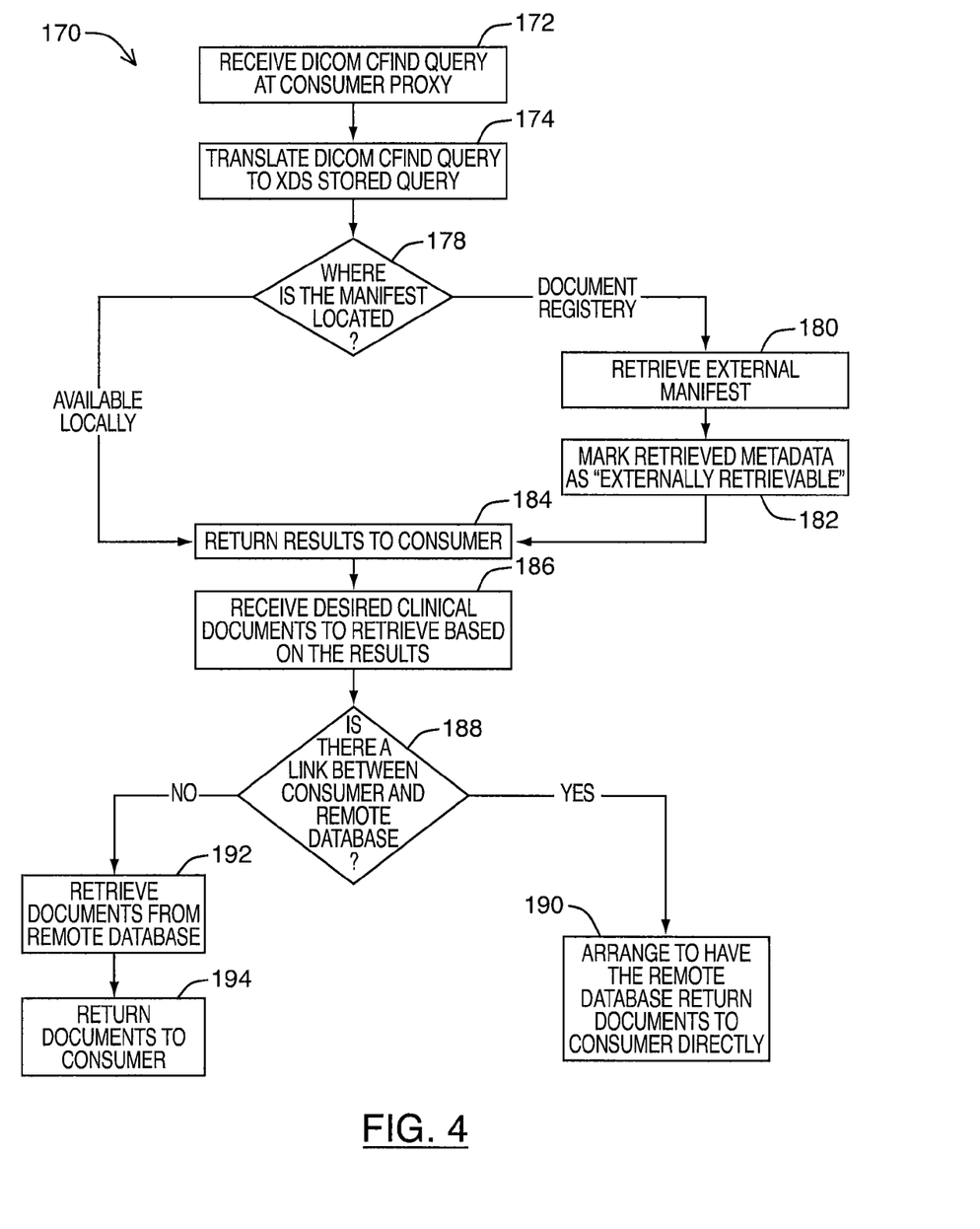
FIG. 4 is flowchart illustrating the steps of a method for processing DICOM query at a consumer proxy to retrieve patient manifests and clinical documents from an XDS database according to the embodiments described herein.

Referring now to FIG. 4, illustrated therein is a computer implemented method 170 performed by a consumer proxy having a processor and a memory to facilitate searching of DICOM objects referenced by XDS patient manifests by a document consumer operating in DICOM standard according to one embodiment of the invention.

Method 170 begins at step 172 wherein the processor receives a DICOM query for one or more DICOM format clinical documents. The method 170 proceeds to step 174 whereby the processor translate the received DICOM query to a XDS stored query. The translation could be implemented by at least some of the steps of method 130 described hereinabove. If the translation is successful, the method 170 proceeds to step 178.

At step 178, the XDS stored query is used to search the manifests contained in remote XDS document registry as well as in the local memory. If relevant metadata associated with the DICOM objects are located locally, then the method 170 proceeds to step 180. If the relevant manifests are not located locally, then the method 170 proceeds to step 181.

At step 180, relevant metadata is retrieved from the local memory. The local memory may contain metadata from previously conducted queries.

At step 181, the relevant manifests are retrieved from a remote document registry. The manifests are not compatible with the DICOM standard being used by the document consumer. The received metadata will be filtered such that only metadata associated with clinical documents that are compatible with or are interested in by the document consumer are selected. That is, the metadata associated with clinical documents referred to in the patient manifest which may be compatible with the DICOM format will be selected to be returned to the document consumer. The method 170 then proceeds to step 182.

At step 182, the metadata associated with the DICOM objects referenced by the manifest may be stored in the memory of the consumer proxy to attempt to facilitate future queries locally. The clinical documents referred to by the stored metadata may be marked as "externally retrievable", and the external addresses where the documents may be retrieved from stored. The method 170 then proceeds to step 184.

In step 184, the results containing metadata associated with one or more DICOM format clinical documents are returned to the document consumer. The document consumer may review the results and select at least one desired clinical document. In some cases, the document consumer may not select any desired clinical document and/or resubmit a new query.

At step 186, the consumer proxy receives a retrieve request indicating desired clinical document based on the results provided in step 185.

At step 188, the consumer proxy determines whether there exists a data link between the document consumer and the remote database where the desired documents are located. If there is a data link, the method 170 proceeds to step 190. If there is no direct link, then the method 170 proceeds to step 192.

At step 190, the consumer proxy will submit a retrieve request and set the document consumer as the return address for the retrieve request such that the remote database returns the desired documents to the document consumer directly ("3-point move").

At step 192, the consumer proxy will submit a retrieve request with the consumer proxy as the return address such that the desired documents are returned to the consumer proxy. The desired documents are then returned to document consumer at step 194.

While the steps of the above methods have been described sequentially hereinabove, it should be noted that sequential performance of the steps may not need to occur for successful implementation of the method. As will be evident to one skilled in the art, rearranging sequence of performance of the steps, omitting the performance of some steps, or performing the steps in parallel may be possible without abandoning the essence of the invention.

While certain features of the invention has been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A computer implemented method of performing at least one document consumer query comprising:
    a) providing a first processor and a memory operatively coupled thereto;
    b) receiving at least one query for at least one clinical document in a first language from at least one document consumer at the first processor, the document consumer having a second processor configured to provide the at least one query to the first processor in the first language;
    c) prior to translating the at least one query into a second language, determining whether differences between the first language and the second language prevent at least a portion of the at least one query from being translated into the second language;
    d) in response to determining that differences between the first language and the second language prevent at least a portion of the at least one query from being translated into the second language, conducting, using the first processor, a best effort transformation to obtain, based on the at least one query, a translated query in the second language, the best effort transformation comprising one or more translations to resolve differences between the first language and the second language, and when the query in the first language comprises a first patient identifier containing at least one wildcard, the best effort transformation further comprises:
        performing at least one of searching the memory for an existing patient identifier that is uniquely linked to the first patient identifier and truncating the at least one wildcard from the first patient identifier, such that a second patient identifier without any wildcards is obtained;
        querying a cross-referencing engine using the second patient identifier to determine whether there is a unique match between the second patient identifier and a third patient identifier in the cross-referencing engine, the cross-referencing engine being adapted to identify and link different patient identifiers associated with a same individual patient; and
        if a unique match is found, including the third patient identifier when translating the query into the second language;
    e) conducting the translated query in at least one database configured to receive queries in the second language by the first processor to obtain a first result; and
    f) providing the obtained first result to the document consumer.

2. The method of claim 1 wherein the first language is compliant with the Digital Imaging and Communications in Medicine (DICOM) standard, and the second language is compliant with Cross-Enterprise Document Sharing (XDS) standard.

3. The method of claim 2 wherein the cross-referencing engine is separate from the first processor.

4. The method of claim 2, wherein when the query contains at least one DICOM attribute constraint, and the best effort transformation of the query into the second language comprises at least one of the following mappings:
    a) direct one-to-one mapping from the at least one DICOM attribute to a corresponding XDS attribute;
    b) concatenating a number of different a plurality of the DICOM attributes to a corresponding XDS attribute;

c) associating the at least one DICOM attribute to a set of values, the result of the association being indicative of a corresponding XDS attribute; and d) specifying a fixed value for the corresponding XDS attribute.

5. The method of claim 2 wherein when the query is for an imaging object, and the database contains metadata about a plurality of clinical documents of various types including imaging objects, conducting the translated query further comprises selecting metadata associated with clinical documents that are imaging documents, the metadata being selected to be returned as the first result.

6. The method of claim 2, wherein when the first results comprises metadata about clinical documents, the method further comprises storing the metadata in the memory such that the metadata is available locally for at least one future query.

7. The method of claim 2, wherein when the first result comprises metadata about clinical documents, the method further comprising:
   a) receiving a retrieve request in the first language for requested clinical documents comprising at least one clinical document from the document consumer based on the first result; and
   b) performing the retrieve request in the second language such that the clinical document requested is provided to the document consumer.

8. The method of claim 7, wherein when the requested clinical documents are stored in at least one database that is remote from the first processor, the method further comprises:
   a) determining whether a data communication link exists between the remote database and the document consumer; and
   b) based on the results of the determination, performing at least one of:
      (i) directing the remote database to return the requested clinical documents to the document consumer directly if the communication link exists, and
      (ii) retrieving the requested clinical documents from the remote database and then providing the requested clinical documents to the document consumer if the communication link does not exist.

9. The method of claim 1 wherein when the database contains objects compatible and incompatible for use with the at least one document consumer, conducting the translated query further comprises selecting compatible objects to be returned as the first result.

10. A physical non-transitory computer readable medium comprising instructions for causing a first computer processor to function as a consumer proxy for processing document consumer queries for patient data in one or more databases, the instructions comprising:
   a) receiving at least one query for at least one clinical document in a first language from at least one document consumer having a second processor configured to provide the at least one query to the first processor in the first language;
   b) prior to translating the at least one query into a second language, determining whether differences between the first language and the second language prevent at least a portion of the at least one query from being translated into the second language;
   c) in response to determining that differences between the first language and the second language prevent at least a portion of the at least one query from being translated into the second language, conducting a best effort transformation to obtain, based on the at least one query, a translated query in the second language, the best effort transformation comprising one or more translations to resolve differences between the first language and the second language, and when the query in the first language comprises a first patient identifier containing at least one wildcard, the best effort transformation further comprises:
      performing at least one of searching the memory for an existing patient identifier that is uniquely linked to the first patient identifier and truncating the at least one wildcard from the first patient identifier, such that a second patient identifier without any wildcards is obtained;
      querying a cross-referencing engine using the second patient identifier to determine whether there is a unique match between the second patient identifier and a third patient identifier in the cross-referencing engine, the cross-referencing engine being adapted to identify and link different patient identifiers associated with a same individual patient; and
      if a unique match is found, including the third patient identifier when translating the query into the second language;
   d) conducting the translated query in at least one database configured to receive queries in the second language by the first processor to obtain a first result; and
   e) providing the obtained first result to the document consumer.

11. A consumer proxy for processing at least one document consumer query comprising:
   a) a first processor;
   b) a memory operatively coupled to the first processor;
   c) wherein the first processor is programmed for:
      i) receiving at least one query for one or more clinical documents in a first language from at least one document consumer, the document consumer comprising a second processor configured to provide the at least one query to the first processor in the first language;
      ii) prior to translating the at least one query into a second language, determining whether differences between the first language and the second language prevent at least a portion of the at least one query from being translated into the second language;
      iii) in response to determining that differences between the first language and the second language prevent at least a portion of the at least one query from being translated into the second language, conducting a best effort transformation to obtain, based on the at least one query, a translated query in the second language, the best effort transformation comprising one or more translations to resolve differences between the first language and the second language, and when the query in the first language comprises a first patient identifier containing at least one wildcard, the best effort transformation further comprises:
         performing at least one of searching the memory for an existing patient identifier that is uniquely linked to the first patient identifier and truncating the at least one wildcard from the first patient identifier, such that a second patient identifier without any wildcards is obtained;
         querying a cross-referencing engine using the second patient identifier to determine whether there is a unique match between the second patient identifier and a third patient identifier in the cross-referencing engine, the cross-referencing engine being adapted to identify and link different patient identifiers associated with a same individual patient; and if a unique match is found, including the third patient identifier when translating the query into the second language;

iv) conducting the translated query in at least one database configured to receive queries in the second language by the first processor to obtain a first result; and v) providing the obtained first result to the document consumer.

12. The consumer proxy of claim 11 wherein the first language is compliant with Digital Imaging and Communications in Medicine (DICOM) standard, and the second language is compliant with Cross-Enterprise Document Sharing (XDS) standard.

13. The consumer proxy of claim 12 wherein the cross-referencing engine is separate from the first processor.

14. The consumer proxy of claim 12, wherein when the query contains at least one DICOM attribute constraint, and the best effort transformation of the query into the second language comprises at least one of the following mappings:
a) direct one-to-one mapping from the at least one DICOM attribute to a corresponding XDS attribute;
b) concatenating a number of different a plurality of the DICOM attributes to a corresponding XDS attribute;
c) associating the at least one DICOM attribute to a set of values, the result of the association being indicative of a corresponding XDS attribute; and
d) specifying a fixed value for the corresponding XDS attribute.

15. The consumer proxy of claim 12 wherein the query is for an imaging object, and the database contains metadata about a plurality of clinical documents of various types including imaging objects, the first processor is further programmed for selecting metadata associated with clinical documents which are imaging documents to be returned as the first result.

16. The consumer proxy of claim 12, wherein when the first results comprises metadata about clinical documents, the first processor is further programmed for storing the first results in the memory such that the metadata is available locally for at least one future query.

17. The consumer proxy of claim 16, wherein when the requested clinical documents are stored in at least one database that is remote from the consumer proxy, the first processor is further programmed for:
a) determining whether a data communication link exists between the remote database and the document consumer; and
b) based on the results of the determination, performing at least one of:
(i) directing the remote database to return the requested clinical documents to the document consumer directly if the communication link exists, and
(ii) retrieving the requested clinical documents from the remote database and then providing the requested clinical documents to the document consumer if the communication link does not exist.

18. The consumer proxy of claim 12 wherein when the first result comprises metadata about clinical documents, the first processor is further programmed for:
a) receiving a retrieve request in the first language for requested clinical documents comprising at least one clinical document from the document consumer based on the first result; and b) performing the retrieve request in the second language such that the clinical document requested is provided to the document consumer.

19. The consumer proxy of claim 11, wherein when the database contains objects compatible and incompatible for use with the at least one document consumer, the first processor is further programmed for selecting metadata associated with the compatible objects to be returned as the first result.

20. A system for processing at least one document consumer query comprising:
a) at least one document consumer operating in a first language having a first processor programmed for submitting at least one query for clinical documents in the first language;
b) at least one document registry operating in a second language incompatible with the first language, the document registry configured to receive queries in the second language and having a memory containing metadata about clinical documents whereby the query is to be conducted;
c) at least one consumer proxy comprising a memory and a first processor coupled thereto, the first processor programmed for:
receiving the query from the document consumer;
prior to translating the at least one query into a second language, determining whether differences between the first language and the second language prevent at least a portion of the at least one query from being translated into the second language;
in response to determining that differences between the first language and the second language prevent at least a portion of the at least one query from being translated into the second language, conducting, using the first processor, a best effort transformation to obtain, based on the at least one query, a translated query in the second language, the best effort transformation comprising one or more translations to resolve differences between the first language and the second language, and when the query in the first language comprises a first patient identifier containing at least one wildcard, the best effort transformation further comprises:
performing at least one of searching the memory for an existing patient identifier that is uniquely linked to the first patient identifier and truncating the at least one wildcard from the first patient identifier, such that a second patient identifier without any wildcards is obtained;
querying a cross-referencing engine using the second patient identifier to determine whether there is a unique match between the second patient identifier and a third patient identifier in the cross-referencing engine, the cross-referencing engine being adapted to identify and link different patient identifiers associated with a same individual patient; and
if a unique match is found, including the third patient identifier when translating the query into the second language;
conducting the translated query in the second language at the at least one document registry to obtain a first result containing metadata about clinical documents; and
providing the first results to the document consumer.

21. The system of claim 20 wherein the first language is compliant with Digital Imaging and Communications in Medicine (DICOM) standard, and the second language is compliant with Cross-Enterprise Document Sharing (XDS) standard.

22. The system of claim 20 wherein the cross-referencing engine is separate from the first.

23. The system of claim 20, wherein when the at least one document registry contains objects compatible and incompatible for use with the at least one document consumer, the first processor is further programmed for selecting compatible objects to be returned as the first result.

24. The system of claim 20, wherein when the requested clinical documents are stored in at least one database remote to the consumer proxy, the first processor in the consumer proxy is further programmed for:
   a) determining whether a data communication link exists between the remote database and the document consumer; and
   b) based on the results of the determination, performing at least one of:
      (i) directing the remote database to return the requested clinical documents to the document consumer directly if the at least one communication link exists, and
      (ii) retrieving the requested clinical documents from the remote database and then providing the requested clinical documents to the document consumer if the at least one communication link does not exist.

* * * * *